United States Patent [19]
Oeftering

[11] Patent Number: 6,003,388
[45] Date of Patent: Dec. 21, 1999

[54] SYSTEM FOR MANIPULATING DROPS AND BUBBLES USING ACOUSTIC RADIATION PRESSURE

[75] Inventor: Richard C. Oeftering, Amherst, Ohio

[73] Assignee: The United States of America as represented by the Administrator of the National Aeronautics and Space Administration, Washington, D.C.

[21] Appl. No.: 08/969,536

[22] Filed: Sep. 17, 1997

[51] Int. Cl.$^6$ ...................................................... B01L 3/00
[52] U.S. Cl. ...................... 73/864.01; 73/432.1; 73/627; 422/100; 422/99
[58] Field of Search .................................... 210/748, 738, 210/188; 209/155, 163; 406/198; 367/137, 138, 191, 99; 422/99, 100; 73/570, 432.1, 61.75, 64.53, 865.5, 627, 864.01, 864.14, 864.73, 597; 310/328, 334; 347/47, 48, 68, 70; 222/420

[56] References Cited

U.S. PATENT DOCUMENTS

| | | | |
|---|---|---|---|
| 3,683,212 | 8/1972 | Zoltan | 310/328 |
| 4,308,547 | 12/1981 | Lovelady et al. | 347/46 |
| 4,383,264 | 5/1983 | Lewis | 347/68 |
| 4,395,719 | 7/1983 | Majewski et al. | 347/68 |
| 4,468,680 | 8/1984 | Martner | 347/68 |
| 4,914,641 | 4/1990 | Dorr | 367/99 |
| 5,520,715 | 5/1996 | Oeftering | 73/335 |
| 5,533,401 | 7/1996 | Gilmore | 73/622 |
| 5,558,837 | 9/1996 | Tsukishima | 422/99 |
| 5,581,286 | 12/1996 | Hayes et al. | 347/71 |
| 5,591,490 | 1/1997 | Quate | 427/457 |
| 5,739,432 | 4/1998 | Sinha | 73/579 |

OTHER PUBLICATIONS

NASA LeRC Technology Open House Handout "Fluid Manipulation by Acoustic Radiation Pressure or Using Sound to Push Water Around" by Richard Oeftering, Sep. 19, 1996.

NASA LeRC Technology Opportunity Paper . . . Combustion & Fluids CF–070–1 . . . "Technology Opportunity" Liquid Manipulation by Acoustic Radiation Pressure by Richard Oeftering, Sep. 19, 1996.

*Primary Examiner*—Hezron Williams
*Assistant Examiner*—Rose M. Miller
*Attorney, Agent, or Firm*—Kent N. Stone

[57] ABSTRACT

The manipulation and control of drops of liquid and gas bubbles is achieved using high intensity acoustics in the form of and/or acoustic radiation pressure and acoustic streaming, generated by a controlled wave emission from a transducer. Acoustic radiation pressure is used to deploy or dispense drops into a liquid or a gas or bubbles into a liquid at zero or near zero velocity from the discharge end of a needle such as a syringe needle. Acoustic streaming is useful in manipulating the drop or bubble during or after deployment. Deployment and discharge is achieved by focusing the acoustic radiation pressure on the discharge end of the needle, and passing the acoustic waves through the fluid in the needle, through the needle wall itself, or coaxially through the fluid medium surrounding the needle. Alternatively, the acoustic waves can be counter-deployed by focusing on the discharge end of the needle from a transducer axially aligned with the needle, but at a position opposite the needle, to prevent premature deployment of the drop or bubble. The acoustic radiation pressure can also be used for detecting the presence or absence of a drop or a bubble at the tip of a needle or for sensing various physical characteristics of the drop or bubble such as size or density.

32 Claims, 6 Drawing Sheets

6,003,388

SYSTEM FOR MANIPULATING DROPS AND BUBBLES USING ACOUSTIC RADIATION PRESSURE

ORIGIN OF THE INVENTION

The invention described herein was made by an employee of the United States Government and may be manufactured and used by or for the government for government purposes without payment of any royalties thereon or therefore.

FIELD OF THE INVENTION

This invention relates to the control and manipulation of contained and uncontained liquids in space applications and on earth. More specifically, the invention relates to non-invasive detection, deployment and control of drops and bubbles in liquids and gases. The manipulation is achieved typically using acoustical radiation pressure and/or acoustic streaming generated by a transducer in, through or around a dispensing needle.

BACKGROUND OF THE INVENTION

Space exploration and other applications with diminished or zero gravity provides unique environments for deployment or dispensing of drops, droplets (small drops) or bubbles. These include experiments in fluid physics, drop physics and droplet combustion. They also include drops of material deployed for containerless processing studies. In these applications, the most common method of deploying a drop or a bubble is to use needles. Often these needles are arranged in matched pairs with the needles being juxtaposed in such a manner as to compensate for the lack of gravitational force. In the absence of gravity, the surface tension of the liquid becomes the dominant force which must be opposed in order to deploy or dispense a drop or a bubble. Inertia of the drop may act to oppose the surface tension when the needles are rapidly retracted. This is satisfactory for relatively large drops and where there is low surface tension relative to the drop's inertia, or where some initial velocity upon deployment of the drop, droplet or bubble is acceptable. The use of a pair of matched needles serves to balance out the surface tension between the two needles so that the drop or bubble separates with no or little initial velocity. Usually, there is some slight miss-match in the wetting or the surface tension characteristics of each needle, as well as slight asymmetries in needles geometry and position. Therefore, when the needles are retracted, the drop tends to stick to one needle more than to the other so that asymmetrical forces are applied upon separation. Furthermore, the motion of the needles must be in perfect symmetry in terms of start time and velocity of retraction. Otherwise the drop will remain in contact with one needle longer than with the other resulting in an undesired initial velocity. Also, the needle retraction must be carried out at high speed in order to maximize the effects of inertia and minimize the effects of any asymmetry in retraction. As the size of the drop decreases to droplet size the mismatch in symmetry becomes even more noticeable, in turn resulting in a higher imparted velocity to the droplet.

All of these variables mean that the deployment apparatus must be designed and precisely tuned for each application. Furthermore, the mechanisms for deployment are intolerant to changes in liquid properties or mechanical flaws. The mechanisms are delicate and easily damaged. For these reasons, the techniques lack flexibility thereby limiting their use as a general purpose tool. Furthermore, in space, a common objective is to deploy a droplet or bubble with zero or nearly zero initial velocity. Failure to deploy the droplet or bubble in this manner often results in an experiment which is deemed a failure.

Earth applications for deployment of drops, droplets and bubbles includes the dispensing of liquids such as adhesives and inks or liquid-solid mixtures such as protective coatings, solder pastes, and also molten metal solders. Many operations such as the manufacture of integrated electrical circuits and circuit boards and the dispensing of drops for medical analysis or treatment or for dispensing of biological specimens for diagnosis or research likewise require precise metering and placement of small quantities of fluids.

There are several methods commonly used for dispensing or depositing of fluids including drop dispensing, jet dispensing, drop-on-demand, and spray deposition.

Drop dispensing uses a simple nozzle or needle to form a drop of liquid displaced from a reservoir using a syringe or other pumping or pressurizing method. For drops that are relatively large in proportion to the needle size, gravity opposed by surface tension determines the ultimate size of the drop. When the gravity force exceeds the surface tension, the drop separates from the nozzle. The properties of surface tension and gravity, as well as the needle characteristics are generally fixed and are not easily changed. Therefore, the ability to change the drop size or to control its deployment on command is not practical. For drops which are relatively small (droplets) compared with the size of the needle, the dispensing systems must make physical contact between the droplet and the surface on which the droplet is to be applied. The wetting and surface tension characteristics of the target surface must exceed the surface tension force between the droplet and the needle to assure complete deployment. The need to place each droplet on the target by physically moving the needle or the target up and down, combined with the need to move the needle or target laterally to the next position, slows down the process, adds mechanical complexity, and requires additional controls.

Jet dispensing causes a high speed jet of liquid to issue from a nozzle. The Rayleigh instability causes the liquid to break up into droplets. External vibration is used to create capillary waves in the surface of the jet. These waves are driven by surface tension and grow in amplitude until individual droplets form. This jet dispensing forms the basic approach for many types of ink jet printing. With its high velocities, jet dispensing does not work well for high viscosity fluids or for visco-elastic fluids. Furthermore, the dispensing of liquid drops or bubbles is impossible at low or zero velocities. Also, the process causes a large number of droplets to emanate from the nozzle, on the order of many thousands of droplets per second. Only a small portion of the droplets collect on the target surface, the rest being recycled for reuse. Thus, the efficiency of the system, based upon the percent of deployed droplets striking the target, tends to be very low.

The drop on demand approach is capable of ejecting individual droplets, using a pressure pulse within a liquid cavity to cause each individual drop to be discharged from an orifice. The velocity of the liquid jet in this type of system is high, because of the necessity of overcoming surface tension at the orifice. This system is satisfactorily used only on low viscosity liquids, with high viscosity or visco-elastic materials being unusable.

Spray deposition is similar to jet dispensing except that the flow is distributed over a wide surface area, where the liquid is allowed to break into droplets. The process is usually accompanied by gas jets to accelerate the break up of the flow into droplets. Spray deposition is the basis for conventional spray painting. The system does not work well with highly vicious liquids or visco-elastic liquids. Often, it is necessary to add thinning agents or solvents to reduce the viscosity of the fluid. This results in high levels of vapors, creating health, environmental, and flammability hazards. Furthermore, the wide distribution of droplet sizes makes the discreet dispensing of precisely sized single droplets in a repeatable manner, impossible.

All of these prior art processes suffer similar drawbacks in that they do not permit the dispensing of droplets at a very low velocity. Furthermore, they do not permit the exercise of control over the size, frequency or characteristics of the individual droplets.

THE SUMMARY OF THE INVENTION

An objective of the present invention is to provide improved performance and reliability in dispensing and deploying liquid drops in a liquid medium or in a gas or vacuum and of gas bubbles in a liquid medium at a zero or nearly zero velocity.

It is another objective of the present invention to precisely deploy or dispense drops or bubbles without reliance upon gravity or the effects of surface tension on earth or in space;

Another object of the present invention is to control and manipulate liquid drops and bubbles with a minimum of mechanical parts, external plumbing and pumping systems and seals;

Yet another objective of the present invention is the precise dispensing of liquid drops and gas bubbles in chemical processing, biomedical applications, and the application of liquid coatings, adhesives, pastes and liquid solders to substrates;

Yet another object of the present invention is the improved performance and reliability over prior art methods, and improved feedback to sense positioning and characteristics of a deployed drop or bubble;

Still another objective of the present invention is the incremental use of acoustic radiation pressure and/or acoustic streaming to control, contain and monitor deployment of drops or bubbles in space or on earth;

Still another objective of the present invention is to adjust power levels of acoustic energy based upon changes in liquid characteristics and surrounding conditions, to control the properties of deployed drops or bubbles.

These objectives are achieved by coupling a conventional dispensing needle with a high intensity acoustic source generating acoustic waves and providing a means of conducting the acoustic waves to the drop where acoustic radiation pressure with or without acoustic streaming causes the drop to separate at zero or low velocity from the needle tip. The needle forms the drop or bubble and the surface tension of the liquid supports the drop prior to placement on the target substrate or solid surface. The acoustic source is coupled by one of three ways, by using the internal fluid within the bore of the needle as a conduit to conduct acoustic waves from the source to the drop at the needle tip, or by using the fluid volume external of the needle to conduct acoustic waves coaxial focused at the drop or bubble at the needle tip, or by using the cylindrical wall of the needle as a solid conductor and transmitter, thus conducting the acoustic waves from the source to the drop or bubble at the needle tip. These approaches my be used individually or combined. Further the inherent ability of the acoustic transducer to sense the position of the drop or bubble may be used to detect the presence of the drop/bubble and determine whether deployment has occurred.

The present invention relates to a method for manipulating a drop of a first fluid in the presence of a second fluid. The process comprises the steps of 1) positioning the drop of the first fluid at the discharge end of a conduit, 2) focusing a source of acoustical radiation pressure on the drop, and 3) causing the pressure to change the relationship between the drop and the discharge end of the conduit. The drop can be a liquid or a gas bubble. When the drop is a liquid, the second fluid can be a liquid, a gas, or a vacuum. When the drop is a bubble, the second fluid is a liquid.

The manipulating of the drop may involve dislodging of the drop from the end of the conduit, either causing the drop to be dislodged at zero or low velocity, or preventing premature release of the drop. Alternatively, it may comprise sensing the physical property of the drop such as the presence or the absence of the drop at the end of the conduit, or the detection of the drop being dislodged. The sensing may be used to detect various physical characteristics of the drop. Acoustical streaming may be employed along with acoustic radiation pressure to assist in the deployment or dislodging of the drop from the end of the needle.

The source of the acoustic radiation pressure typically is a piezoelectric transducer. The method involves the transmission of acoustic radiation pressure to the drop through the first fluid in the conduit; or through the wall of the conduit itself. Another alternative is to transmit the pressure from an annular transducer to the drop through the second fluid coaxially surrounding the conduit. Yet another choice is to place the transducer at a location remote from the conduit, and in axial alignment therewith, and to focus the energy on the drop through the second fluid.

The drop may be discharged from the conduit at zero or low discharge velocity by empirically using discrete pressure bursts of acoustic radiation pressure, gradually increasing the duration of each successive burst until the surface tension between the discharge end and the drop is exceeded. Likewise, the duration of the bursts can be selectively or randomly altered to adjust for various drops sizes.

Pulsing of the acoustic radiation pressure can be used to cause the drop to oscillate. The oscillation can alternatively be used to determine properties of the drop or to effect discharge of the drop. Conversely, the acoustic radiation pressure can be used to suppress externally induced oscillations within the drop.

The method may be conducted in a gravity-free environment, or in a normal earth environment.

The invention also includes a process for using acoustic radiation pressure for sensing of a drop. The process comprise the steps of a) focusing an acoustic transducer on a target, b) emitting a single wave or a burst of acoustic radiation of finite duration from the transducer, c) gathering reflected the acoustic wave or waves from the target, and d) analyzing the reflected wave form. The transducer is typically focused on the discharge end of a needle containing a first fluid, said discharge end being surrounded by a second fluid. The reflected waves are then analyzed to determine the presence or absence of a drop at the discharge end of the needle. Alternatively, the target may be a drop of the first fluid in a second fluid, whereupon the reflected waves are analyzed to determine the physical properties of the drop.

The invention also comprises an apparatus for deploying discrete drops of a first fluid into a second fluid using acoustic radiation pressure for deployment. The apparatus comprises a tubular needle to conduct the fluid, an acoustical transducer, along with means to focus acoustic energy therefrom at the dispensing end of the needle, a housing to support the transducer, and suitable electrical connections to transmit an electrical signal to the transducer. The needle comprises a dispensing end from which the drop is deployed, and a coupling end. The housing provides a sealed containment for the fluid, and is in fluid communication with the coupling end of the needle. The electrical signal originates in a signal generator circuit which includes a radio frequency power amplifier circuit. The amplifier circuit may also utilize a network to match the impedance of the amplifier circuit with that of the transducer. The apparatus may also include an acoustic feedback signal for purposes of acoustic sensing.

The transducer is acoustically coupled to the coupling end of the needle, and the needle includes a tapered internal bore from a larger bore at the coupling end to a smaller internal bore at the dispensing end. Alternatively, the transducer can be acoustically coupled to the second fluid coaxially surrounding the needle, and is focused at the dispensing end of the needle. Yet another choice is for the transducer to be acoustically coupled to the discharge or dispensing end through the first fluid in the bore of the needle.

In yet another alternative, the transducer can be positioned at a location remote from the conduit and in axial alignment therewith. The transducer is acoustically coupled with the second fluid to transmit acoustic energy which is focused at the discharge end of the conduit. In a variation of this, an annular transducer may be used coaxially around the needle to transmit acoustic energy toward a drop at the discharge end of the needle, and through the second fluid along the needle. Another transducer may be positioned at a remote location opposing the first transducer and in axial alignment with the first transducer and the needle. The two transducers can then be used to control the deployment of the drop from the end of the needle and then to manipulate the drop along the common axis of the transducers.

BRIEF DESCRIPTION OF THE DRAWINGS

Reference is now made to the accompanying drawings in which.

DETAILED DESCRIPTION OF THE INVENTION

The purpose of the present invention is to control, manipulate or analyze fluid drops by using a transducer that produces high acoustic waves therefore creating a force called acoustic radiation pressure and a non-linear effect called acoustic streaming. The acoustic streaming, also known as acoustic wind or quartz wind accompanies the application of high intensity sounds in gases and liquids. A more detailed discussion of the theories and nature of acoustic streaming are presented in the text entitled "High Intensity Ultra Sonic Fields" edited by L. D. Rosenberg, printed by Plenum Press in 1971.

Figure 1:
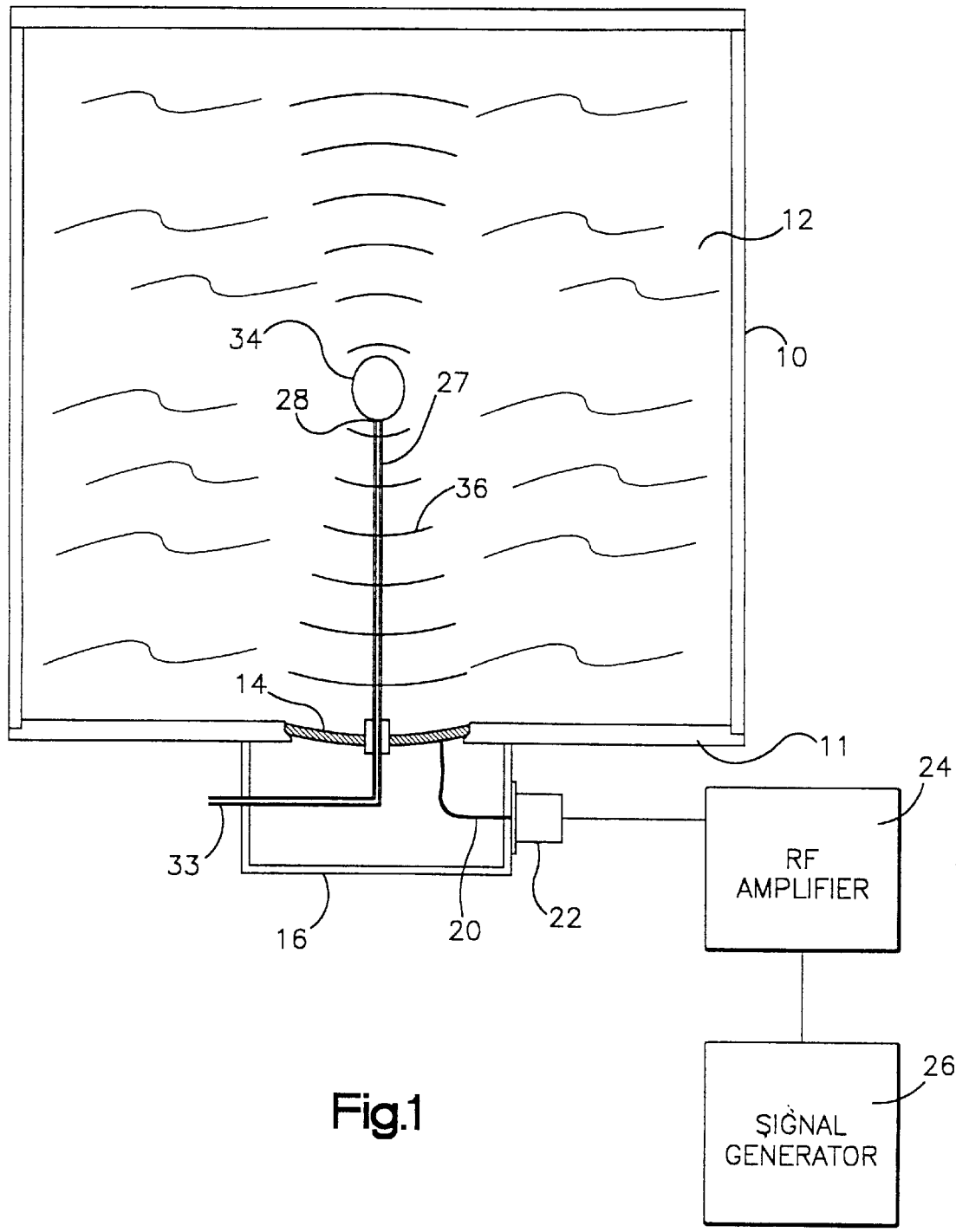
FIG. 1 is a perspective elevational view of a liquid cell, liquid dispenser, transducer and associated circuitry.

An acoustic radiation pressure, bubble/drop deployment cell 10 containing a fluid mass 12 is shown in FIG. 1. A transducer 14 is mounted in the wall 11 of the cell in communication with the fluid 12. A coaxial electrical connector 20 joins the transducer through a radio frequency (RF) connector 22 such as a BNC connector to a radio frequency amplifier 24. This in turn is connected to an electrical signal generator 26. The generator can be a computer, a microprocessor or a manual button, switch or relay under the control of the user.

The transducer is made from a suitable piezoelectric material. Included among commonly known piezoelectric materials are single crystal materials such as quartz and lithium niobate polycrystalline ceramic material such as lead zirconium titanate, and various amorphous polymeric crystals materials such as polyvinylidine fluoride. The piezoelectric material is typically plated with a layer of chrome followed with a layer of gold to produce a highly conductive surface. Quartz crystals typically require relatively high voltage up to about a 1,000 volts whereas crystals of leads zirconium titanate or lithium niobate require a voltage in the range of 30 to 100 volts. As an alternative to piezoelectric materials to drive the transducers, the invention also contemplates the use of mechanical and/or magnetostrictive energy sources.

The practice of the present invention involves the use of a needle 27 such as a syringe needle having a tubular structure through which a first fluid is conducted from fluid connection 33. The length of the needle extending into the fluid mass can vary widely from very high length to diameter ratio greater than 20/1 to a length which is so short that the needle acts as an orifice or aperture. The internal bore of the needle should be free of obstructions to permit the unimpeded transmission of liquid and ultra-sonic vibrations.

The dispensing end 28 of the needle is normally square-cut, perpendicular to the axis of the tube. However, other end arrangements such as an outward flared or bugle shaped tip or a tapered end may be used. The shape has an effect on the amount of surface area available for the surface tension of the drop to act on. An outward flare helps stabilize the drop from vibration if the drop has relatively low surface tension and viscosity. The tapered end helps minimize surface tension if the drop has high tension or viscosity. A drop or bubble 34 of the first fluid is shown at the discharge end 28 of the needle.

Figure 2:
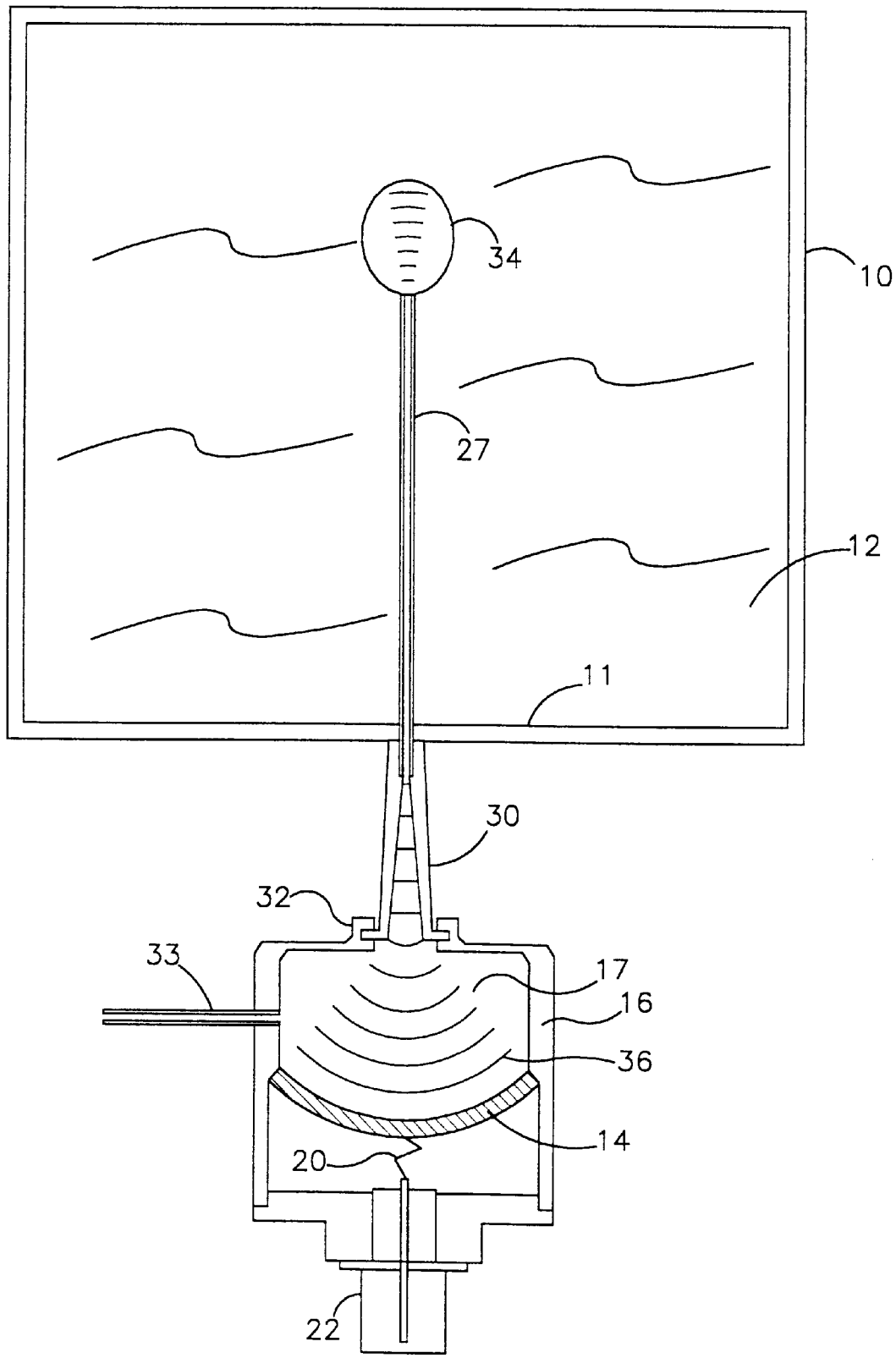
FIG. 2 is an elevational view of a needle for the transmission of liquid and acoustic radiation through the inner bore of the needle.

FIG. 2 shows a housing 16 containing a first fluid 17, a deployment cell 10 containing a second fluid 12, and a needle 27 in fluid communication with the housing and the cell. The second fluid can be a liquid, a gas, or a vacuum. The needle extends through a wall 11 of the deployment cell and is joined to an adapter 30 which is coupled by a bayonet-type coupling such as a Luer-Lok® connector to the housing. Fluid enters the housing 16 through fluid connection 33. Acoustic waves 36 generated by transducer 14 pass through the fluid 17 in the housing 16 and travel through the adapter into the needle, converging in bubble or drop 34 at the discharge end of the needle. A coaxial electrical connection 20 joins the transducer by a BNC or other connector to a signal generator and amplifier (not shown) of the type described in FIG. 1. The adapter serves as an acoustical coupling. It has a tapered internal bore that accommodates the transmission of the first fluid into the needle without abrupt steps or discontinuities that could cause acoustic reflections or that would otherwise inhibit the transmission of sound waves. A satisfactory reduction ratio of about 3 to 1 has been found to work well, using an adapter with a 0.9 mil inlet opening and a 0.3 mil outlet.

The acoustical transducer 14 is mounted within an acoustic housing 16 which provides support for electrical connection 20. The housing is shielded to contain the radio frequency electromagnetic emissions that occur at the high frequencies generated by the transducer 14.

Focusing of the transducer is needed to assure that the acoustic energy (shown as waves 16) is delivered to the end of the needle. The transducer may have an inherently spherical design that focuses the energy, a common design for ceramic transducers or materials that are not single crystal in nature. However, for single crystal transducers in which the acoustic wave is generated along a single axis, it is important to use a focusing lens to focus the acoustic energy.

The taper of the adapter 30 acts as a further focusing device for transmitting sound into the needle. For high quality lenses with surface variations less than perhaps 1/10th of a wave length, the theoretical focus is defraction limited. In this case the focal diameter will be as small as approximately a single acoustic wave length. A typical syringe needle has a size from 19 to 26 gauge which is smaller than the defraction limited focus of a transducer of 1 megahertz or less. Therefore, the tapered adapter further focuses the acoustic waves beyond the capacity of the acoustic lines.

The housing 16 has a port or connection 33 to permit the introduction of the dispensing fluid into the volume formed by the housing, the coupling and the needle. A vent port (not shown) may also be included to bleed off any trapped gas which would interfere with the transmission and focusing of acoustic waves. The source of the fluid may be a fluid container with the means of pumping fluid into the apparatus and forming the drop or bubble. A mechanical pump or a valve regulated pressurization system may be used. A positive displacement device like a piston or a syringe provides both flow rate control and volume control while maintaining very good drop/bubble size control.

The electrical connection 20 to the housing 16 uses a conventional radio frequency coaxial and a BNC-type connector. Internally the leads may be simple non-coaxial provided the housing is grounded and is electromagnetically shielded. Although shielding is not required to drive the transducer, it does minimize the effect of high power radio waves interfering with the control portion of the circuit or other nearby equipment.

The transducer is driven by an electrical circuit capable of emitting a signal at the fundamental frequency of the acoustic transducer or its harmonics with enough power to cause the transducer to create the high intensity effects of radiation pressure and acoustic streaming. The maximum capacity of the transducer is based on its size and the electrical voltage and power limitations of the particular piezoelectric material used for the transducer.

As shown in FIG. 1, the electrical signal originates from a signal generator 26. Normally the signal is of a single frequency and matches the fundamental frequency of the transducer or the odd harmonics thereof. The signal generator must be capable of providing electrical tone bursts, of finite duration. In addition, the signal generator should be capable of providing a single pulse output equal to one wave length or less. The single pulses may be used to detect drop deployment when acoustic feedback is utilized. Because most signal generators are of low power, a radio frequency power amplifier is commonly utilized. The amplifier must be capable of driving the frequencies of the signal generator without distortion of the signal. The gain from the amplifier will be based upon the desired amplitude required to drive the transducer. For some transducers, only positive signals are used whereas with other transducers such as single crystal transducers, fully alternating sinusoidal signals may be utilized.

In the event that the impedance of the transducer differs from the impedance of the radio frequency amplifier, an impedance matching network can be used to assure efficient delivery of power to the transducer.

Acoustical sensing may be used for feedback. The transducer deploying the drop or bubble may also emit acoustic pulses to detect the presence or absence of the droplet. The transducer is capable of converting electrical energy to acoustic energy; conversely it can convert acoustic energy into electrical energy. This enables the transducer to sense the reflection of an acoustic wave or waves. A circuit that is commonly used for acoustic or ultrasonic testing may be employed to detect the electrical response to the reflected waves, and may present or display them for the operator's use or for a computer control system. A monitoring apparatus such as an oscilloscope or a high speed data acquisition system may be used to monitor both the emitted signal and the reflected signal. The acoustic energy used for sensing is much lower than that needed for deployment or dispensing of the fluid. Accordingly, detection or sensing can occur without inadvertently deploying a drop or bubble.

Sensing can be used to detect the presence or absence of a drop or bubble to determine whether the system is ready to deploy or dispense. Furthermore, the sensing can be utilized to correct for failures in bubble or drop formation or deployment. In addition, the sensing can be used to detect subtle differences such as variations in the size and change of fluid properties of the drop or bubble. The acoustic feedback signal for sensing may be analyzed for various characteristics. A simple round trip time of a single pulse may be compared with a known no drop present round trip time characteristic or a drop present formed drop round trip time characteristic.

By pulsing at a high rate, and analyzing acoustic signal for cyclical changes in round trip time, the system may detect if the drop or bubble is oscillating. Furthermore, the nature of the oscillation frequency and the damping rate may be used to characterize the drop size and liquid properties. This in turn can be used for process control.

The amount of acoustic signal attenuation may be used to detect the drop by measuring and comparing the amplitude differences with the "no drop present" condition having a higher reflected signal strength than the "drop present" condition. The "drop present" condition will attenuate the signal because of the slightly longer travel time and the fact that only a portion of the acoustic signal is reflected back into the needle.

The procedure for deploying a drop or bubble from the end of a needle is generally carried out in the following sequence, 1. The first step is to assure that the needle is properly positioned for deployment. In some cases, a fixed needle position will be used while in other cases an initial position will be followed by retraction of the needle to assist in deployment. 2. Before the drop is formed, the system itself or the operator should determine visually or by acoustic sensing if a drop or bubble is present. 3. The formation of the drop requires that the fluid be pumped or displaced from its source to the needle tip. The coupling volume, the supply line and the needle volume must be filled with the fluid without voids or bubbles. The flow rate must be low enough to prevent inertia and to preclude the fluid dynamic forces from exceeding the surface tension of the drop or bubble to be formed. As the drop or bubble approaches the desired size, the flow is halted, but not so abruptly that the system pressure transients or oscillation causes the drop or bubble to be deployed prematurely. 4. Prior to deployment or dispensing, the bubble/drop presence and its condition may be verified. If acoustic sensing is used, then low power pulses or short bursts are used to drive the transducer to emit a sensing wave. The signal generator and the amplifier may be used for pulse emission. Both the emitted signal and the reflected signal are monitored by an operator or a high speed data acquisition system. The monitoring apparatus may be an oscilloscope that monitors a line between the amplifier and the transducer. 5. The parameters of the tone bursts are set for the specific drop/bubble. These parameters include frequency, wave shape (usually a simple sinusoidal wave), signal amplitude and burst duration. If a separate amplifier stage is required, then the gain on the amplifier is adjusted to convert the signal to the appropriate voltage amplitude. 6. The signal generator is commanded to issue an electrical tone burst. The signal typically is amplified by the radio frequency amplifier. The electric signal passes through the impedance match network and drives the acoustic transducer that creates a corresponding acoustic signal. The acoustic waves are focused at the tapered coupling between the transducer and the needle. The waves conduct down the fluid within the bore of the needle to the drop/bubble at the tip of the needle. The acoustic waves are conducted through the drop and impinge on the opposite side of the drop or bubble. The waves reflect from the far side creating an area of acoustic radiation pressure. The force causes the drop to elongate and finally separate from the needle. Alternatively, the initial elongation may not cause separation but an oscillation of the drop and subsequent change in surface tension can cause a drop to separate. Acoustic streaming occurs but is not believed to be a dominant factor in drop deployment at this point. 7. Acoustic sensing may again be used to detect the presence of the droplet. This permits the operator to determine if successful deployment of the drop or bubble has occurred. If the drop is still present at the tip of the needle, then the operator may re-attempt to deploy the drop or bubble. This may be done by increasing the signal energy or the duration of the tone burst or other acoustic parameters that may be used to increase likelihood of deployment. The use of acoustic sensing and parameter adjustments may be performed manually or automatically. Once the bubble or droplet is deployed, the needle may be retracted or be moved to the next dispensing point.

FIG. 3 shows an alternate method for deploying of drops and bubbles in liquids, using a coaxial arrangement. In this embodiment, an annular transducer 14 is mounted in housing 16 external to the dispensing needle 27. The transducer is focused either intrinsically or by use of a focusing lens at a drop or bubble 34 of a first fluid at the tip of the needle. High intensity acoustic waves 36 create acoustic radiation pressure on the external surface of the bubble or drop. Furthermore, the second fluid 12 in the vicinity of the bubble or the drop experiences acoustic streaming. This streaming effect is most pronounced at the focal point of the transducer, and creates a fluid dynamic force that assists in deployment. The deployment with an external coaxial arrangement utilizes a combination of acoustic radiation pressure and acoustic streaming. As in FIG. 2, the transducer 14 is connected by a coaxial electric connection 20 through a BNC 22 or similar connector to an amplifier and a electrical signal generator (not shown). The first fluid is introduced into the needle through fluid connection 33. The transducer is affixed in housing 16 which is mounted in the side walls 11 of the bubble deployment cell.

When deploying a drop of liquid within another liquid, the acoustic properties of the two liquids may be very similar. For this reason, the interface between the liquids is only partially reflective and consequently the formation of radiation pressure within the drops may be insufficient to cause deployment. Therefore, acoustic streaming may become the dominant deployment mechanism.

The use of coaxial deployment permits the focal length of the transducer to be readily adjusted along the axis of the needle to permit tracking of a deployed drop or bubble. The focusing may be accomplished by the use of a plurality of transducers in a phased array, each transducer made up of individual elements that are driven separately but under common control. The acoustic waves may be phased shifted to cause the waves to coalesce at a predetermined focal point. By manipulating the phase arrangement electronically, this focal point can be moved. Either a two dimensional phased array or a three dimensional pattern can be used to provide the wide latitude of flexibility in manipulating the position of the drop or bubble after deployment or in detecting the location of the drop or bubble.

FIG. 4 shows the use of the solid wall of the needle as the conductor of acoustical radiation energy. In this embodiment, an annular transducer 14 is directly coupled to the coupling end 29 of the hollow needle 27. A bubble 34 of a first fluid is shown at the discharge end of the needle. As before, the housing 16 for the transducer is mounted in the wall 11 of the bubble deployment cell. The transducer is connected by wires 20 through a BNC connector or other type of RF to the signal generator and amplifier (not shown). The first fluid is introduced into the needle through fluid connection 33. Focused waves generated by the transducer are introduced into the needle and travel along the cylindrical axis of the needle toward the dispensing or discharge end 28. Here the acoustical radiation waves enter the drop or bubble at the tip of the needle. Focusing of the transducer waves is achieved by tapering the needle. This embodiment is particularly preferable for use when a liquid is being dispensed into a gas or a vacuum environment. The use of the solid wall of the needle as a wave guide serves to minimize loss of acoustic energy to the surrounding environment.

Referring now to FIG. 5, therein is shown an acoustic transducer in axial alignment with the needle, useful for suppressing the early deployment of a drop or a bubble of a first fluid from the end of a needle. As before, the needle 27 has a discharge end 28 on which is disposed a bubble 34. The transducer 14 in housing, 16 transmits a plurality of focused waves 36 which through acoustic radiation pressure serves to maintain the bubble 34, with or without the benefit of acoustic streaming, at the discharge end 28 of the needle. The needle is held in the wall 14 of the bubble deployment cell by a needle holder 31. When using a nonwetting needle, the surface tension between the drop and the liquid in the needle is the only force keeping the drop in contact with the needle. This may be insufficient to prevent premature deployment of the bubble to gravity, or to other forces such as electrostatic or fluid dynamic forces. Therefore, the surface tension cannot be relied upon to control deployment. For this reason, the acoustic radiation pressure is deployed from a position opposite the directional flow of the fluid to the needle. To further assist in stabilizing the drop or the bubble at the discharge end of the needle, the discharge end may be equipped with a ring or an expanded tip flare such as a bugle to hold the bubble or drop against the effects of the acoustic radiation pressure. The drop or bubble then remains trapped between the forces created by the transducer and the stabilizing feature of the needle. The acoustic beam may use continuous waves or employ tone bursts to prevent the drop from deploying inadvertently. To deploy or dispense the drop or bubble, the acoustic radiation is either discontinued or is decreased, whereupon an external force such as gravity causes the bubble or drop to separate. This embodiment is also useful in counteracting the premature deployment of drops or bubbles from the tip of a needle caused by factors such as external vibrations, noise and other disturbances.

Figure 3:
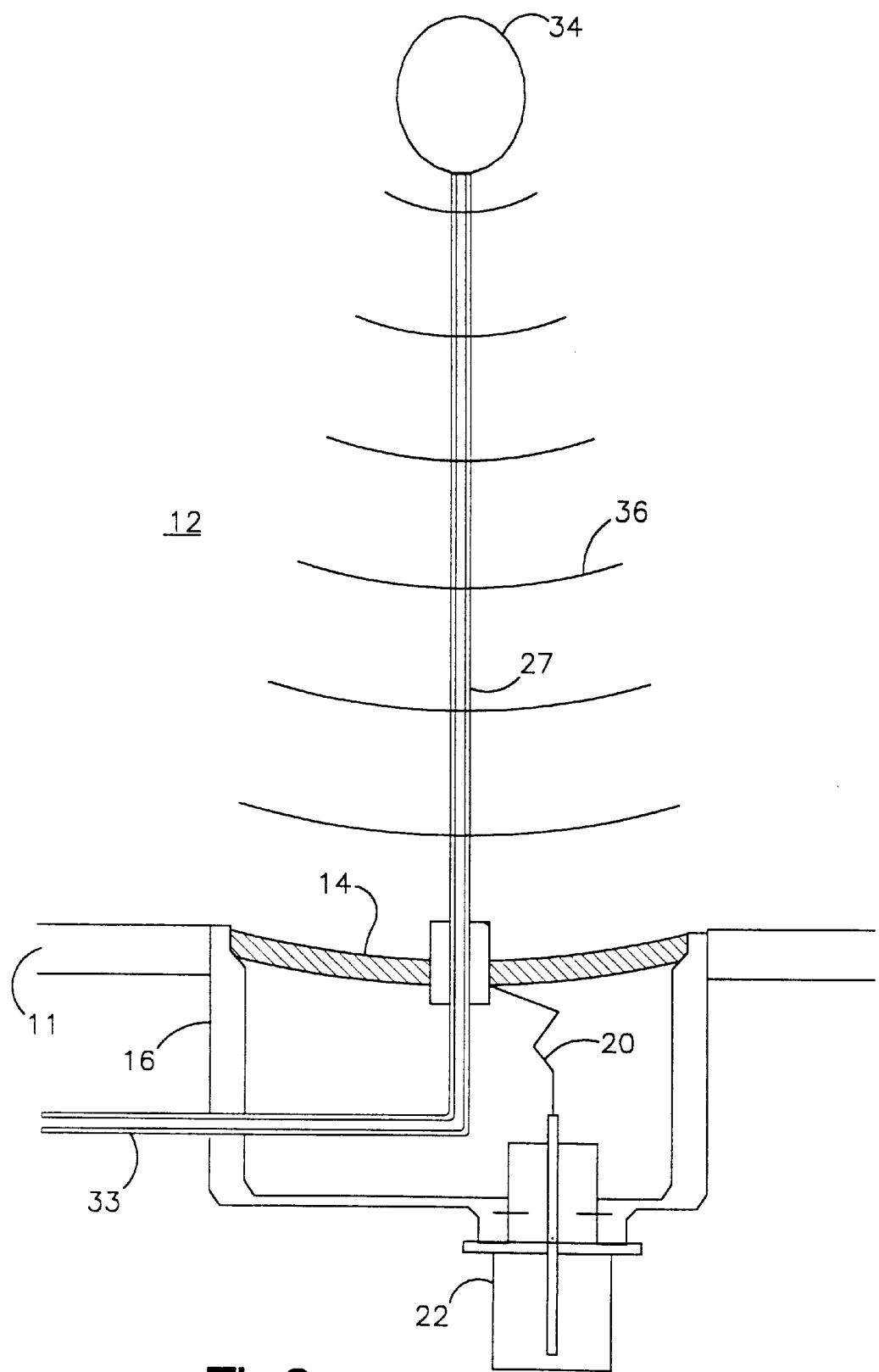
FIG. 3 is an elevational view showing a transmission of a drop or bubble through a needle with coaxial-acoustical radiation.
Figure 4:
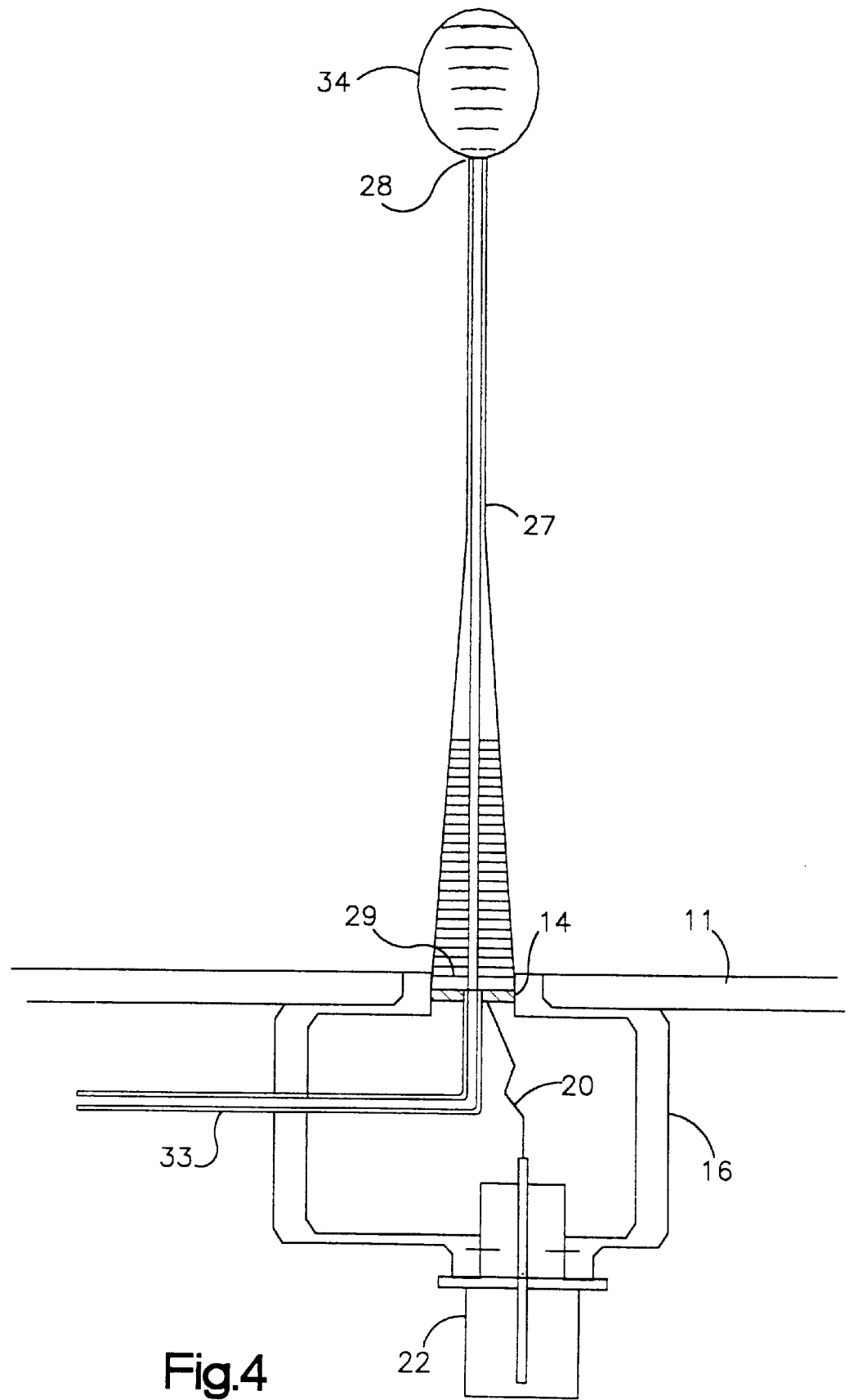
FIG. 4 is an elevational view showing the use of the solid wall of a needle as an acoustical energy conductor.
Figure 5:
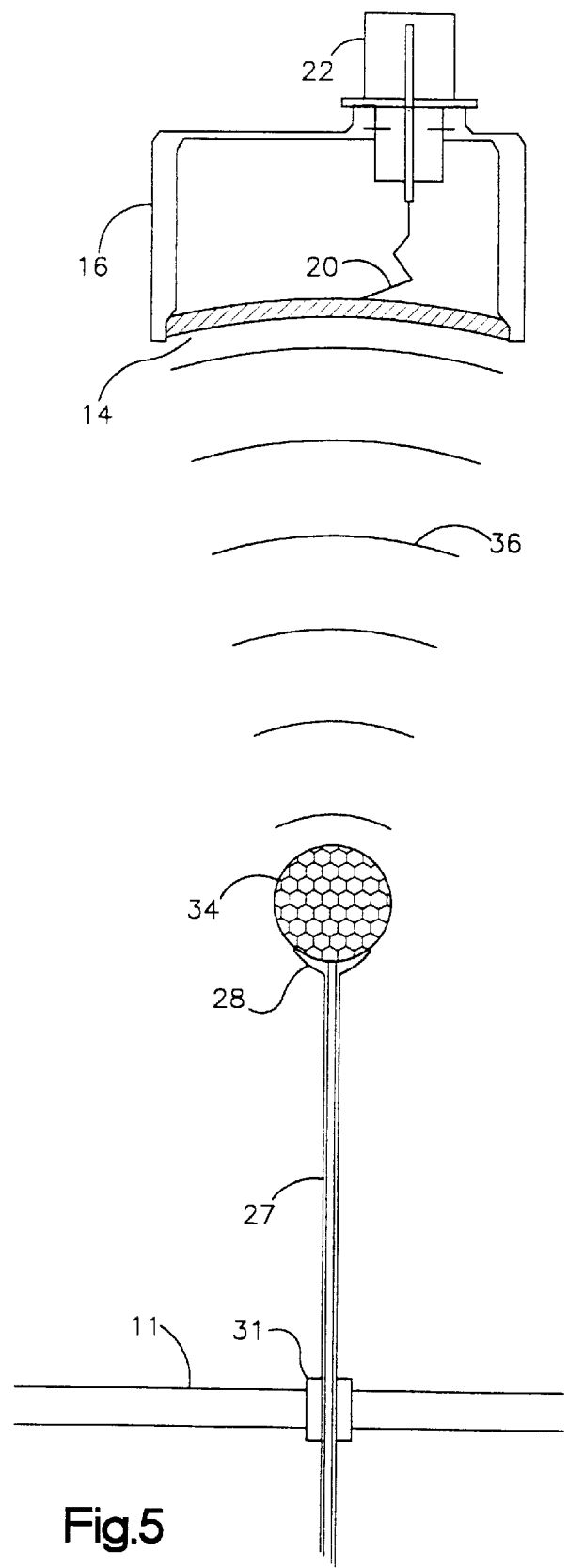
FIG. 5 is an elevational view showing the use of acoustical radiation pressure to counter or suppress the deployment of a bubble or a drop.
Figure 6:
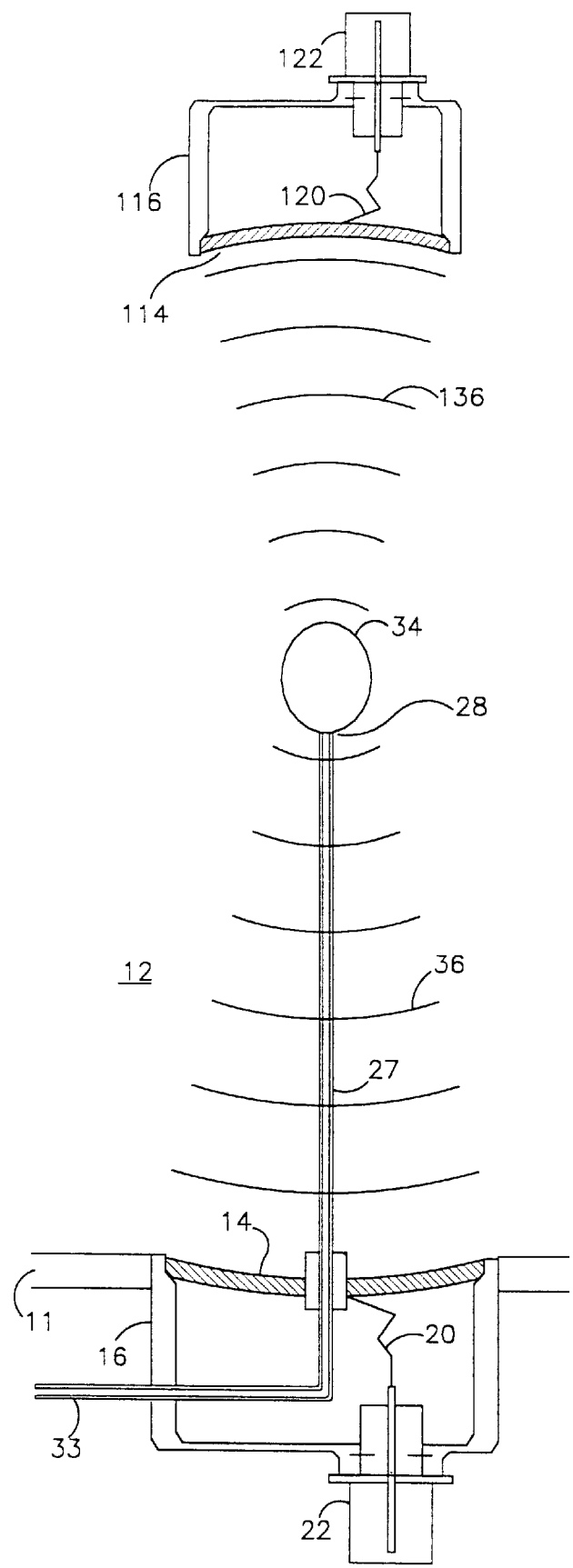
FIG. 6 is an elevational view showing the use of counter and coaxial acoustical radiation pressure on a bubble or a drop.

The embodiment shown in FIG. 3 and in FIG. 5 are combined in FIG. 6 to take advantage of the effects of a coaxial transducer and the counter pressure offered by a counter deployment transducer. A drop or bubble 34 of a first fluid is deployed in a second fluid 12 from the discharge end 28 of needle 27. An annular transducer 14 is mounted in housing 16, mounted in the wall 11 of a deployment cell, as previously described. Waves 36 of acoustic radiation from this coaxial transducer are focused on the bubble 34. In axial alignment with the first transducer is a second transducer 114; mounted in housing 116. The transducer is electrically connected by coaxial cable 120 to a connector 122, and thence to a computer controlled signal generator.

A drop or bubble 34 is deployed in the liquid medium 12 from the discharge end 28 of the needle. The counter deployment transducer then produces waves 136 of acoustic radiation pressure with or without acoustic streaming to control the forward motion or drift of the drop or bubble. This can be done either by continuous or alternating bursts from the opposed transducers, thereby serving to trap the bubble or drop in a given position. The needle can then be retracted from the medium and any disturbance that would otherwise result from the retraction can be counteracted by the counter-deployed transducer. The acoustic radiation pressure and acoustic streaming of the opposed transducers can be manually or automatically controlled separately or together thereby permitting control over the droplet or the position or movement of the drop or bubble within the fluid mass 12.

While the invention has been described in combination with embodiments thereof, it is evident that many alternatives, modifications, and variations will be apparent to those skilled in the art in light of the foregoing teachings. Accordingly, the invention is intended to embrace all such alternatives, modifications and variations as fall within the spirit and scope of the appended claims.

What is claimed is:

1. A method for manipulating a drop of a first fluid at the discharge end of a conduit comprising:
    a) positioning the drop of the first fluid at the discharge end, in the presence of a second fluid
    b) focusing a source of acoustical radiation pressure on the drop, and
    c) causing the acoustical radiation pressure to change the relationship between the drop and the discharge end of the conduit.

2. The method according to claim 1 wherein the drop is a liquid and the second fluid is selected from the group consisting of a liquid, a gas and a vacuum.

3. The method according to claim 1 wherein the drop is a gas bubble, and the second fluid is a liquid.

4. The method according to claim 1 wherein the manipulation includes the use of acoustical radiation pressure to dislodge the drop from the discharge end at a near zero velocity.

5. The method according to claim 1 wherein the manipulation further includes acoustical streaming to assist in changing the relationship between the drop and the discharge end of the conduit.

6. The method according to claim 1 wherein the source of acoustical radiation pressure is a piezoelectric transducer.

7. The method according to claim 6 wherein the conduit is filled with the first fluid and the acoustical radiation pressure is transmitted to the discharge end of the conduit through the first fluid in the conduit.

8. The method according to claim 6 wherein the acoustic radiation pressure is generated in a transducer positioned at a location remote from the conduit and in axial alignment therewith, and passes through the second fluid to the drop.

9. The method according to claim 8 wherein the acoustic radiation pressure controls the drop following dispensing from the discharge end of the conduit.

10. The method according to claim 6 wherein the piezoelectric transducer is focused on the drop at the discharge end of the conduit, and the acoustic radiation pressure is transmitted to the drop through the second fluid surrounding the conduit.

11. The method according to claim 10 wherein the piezoelectric transducer is annular.

12. The method according to claim 1 wherein the drop is manipulated in a zero gravity environment.

13. A method according to claim 1 wherein the drop is discharged from the conduit at a low discharge velocity by empirically using acoustic radiation pressure bursts of increasing duration until surface tension between the discharge end of the conduit and the drop is exceeded.

14. The method according to claim 1 wherein drops of differing sizes are dispensed from the discharge end of the conduit by the use of acoustic radiation pressure bursts of differing durations.

15. The method according to claim 1 wherein pulsing of the acoustical radiation pressure is used to cause the drop to oscillate.

16. The method according to claim 15 wherein oscillation of the drop causes the drop to dislodge from the discharge end of the conduit.

17. The method according to claim 16 wherein the oscillation of the drop is analyzed to determine the physical properties thereof.

18. The method according to claim 1 wherein the acoustic radiation pressure is used to suppress externally induced oscillations within the drop.

19. The method according to claim 1 including the further step of using acoustic radiation pressure to sense a physical property of the drop.

20. An apparatus for deploying drops of first fluid into a second fluid, the apparatus comprising a tubular needle to conduct the first fluid, said needle comprising a fluid dispensing end and a fluid coupling end; an acoustic transducer; an acoustic housing to support the transducer and to provide containment for the first fluid, the housing in fluid communication with the coupling end of the needle; electrical connection between the acoustic transducer and an electrical signal, means to transmit acoustic energy from the transducer to the dispensing end of the needle, and means to generate the electrical signal to cause the focused acoustical energy to deploy the drops.

21. The apparatus according to claim 20 wherein the electrical signal originates in a signal generator circuit.

22. The apparatus according to claim 21 wherein the signal generator circuit includes a radio frequency power amplifier circuit.

23. The apparatus according to claim 22 wherein the radio frequency power amplifier circuit includes a network to match the impedance of the amplifier circuit with that of the transducer.

24. The apparatus according to claim 20 further including an acoustic feedback signal for purposes of acoustic sensing.

25. The apparatus according to claim 20 wherein the needle includes a bore which has a smooth inner diameter and the transducer is adapted to be acoustically coupled to the fluid in the bore.

26. The apparatus according to claim 20 wherein the transducer is acoustically coupled to the coupling end of the tubular needle, and includes a tapered internal bore which tapers from a larger bore at the coupling end to a smaller internal bore toward the dispensing end.

27. The apparatus according to claim 20 wherein the transducer is adapted to be acoustically coupled to the second fluid surrounding the needle, and to be focused at the dispensing end of the needle.

28. A method for manipulating a drop of a first fluid at the discharge end of a conduit comprising:
   a) positioning said drop of first fluid at the discharge end in the presence of a second fluid;
   b) generating acoustic radiation pressure in a transducer positioned at a location remote from the conduit and in axial alignment therewith;
   c) focusing a source of acoustical radiation pressure on the drop; and
   d) passing the acoustic radiation pressure through the second fluid to prevent premature dispensing of the drop.

29. A process for using acoustic radiation pressure for sensing, the process comprising:
   a) focusing an acoustic radiation transducer on the discharge end of a needle containing a first fluid, said discharge end surrounded by a second fluid;
   b) emitting a burst of acoustic radiation of finite duration from the transducer;
   c) gathering reflected acoustic waves from the target; and
   d) analyzing the reflected acoustic waves to determine the presence or absence of a drop of the first fluid at the discharge end of the needle.

30. An apparatus for manipulating drops of a first fluid in the presence of a second fluid, the apparatus comprising a tubular needle to conduct the first fluid, said needle comprising a fluid coupling end and a fluid dispensing end; an acoustic transducer positioned at a location remote from the needle and focused at the dispensing end thereof, an acoustic housing to support the transducer; electrical connection between the acoustic transducer and an electrical signal, and means to transmit acoustic energy from the transducer through the second fluid to the fluid dispensing end of the needle.

31. The apparatus according to claim 30 wherein the acoustic transducer is in axial alignment with the fluid dispensing end of the needle.

32. The apparatus according to claim 31 including a second acoustical transducer coaxially surrounding the fluid dispensing end of the needle and focused at the dispensing end thereof, an acoustic housing to support the second transducer, and means to generate an electrical signal to transmit acoustic energy through the second transducer to the dispensing end of the needle in an axial direction opposed to the direction of the acoustical energy of the first transducer.

* * * * *